US00PP24660P3

(12) United States Plant Patent
Coiner

(10) Patent No.: US PP24,660 P3
(45) Date of Patent: Jul. 22, 2014

(54) FLORIBUNDA ROSE PLANT NAMED 'ISLE OF VIEW'

(50) Latin Name: *Rosa hybrida*
Varietal Denomination: Isle of View

(76) Inventor: James W. Coiner, Covina, CA (US)

( * ) Notice: Subject to any disclaimer, the term of this patent is extended or adjusted under 35 U.S.C. 154(b) by 39 days.

(21) Appl. No.: 13/573,342

(22) Filed: Sep. 10, 2012

(65) Prior Publication Data

US 2014/0075614 P1 Mar. 13, 2014

(51) Int. Cl.
*A01H 5/00* (2006.01)

(52) U.S. Cl.
USPC ..... Plt./151

(58) Field of Classification Search
USPC ..... Plt./151
See application file for complete search history.

*Primary Examiner* — Annette Para
(74) *Attorney, Agent, or Firm* — Christie, Parker & Hale, LLP

(57) ABSTRACT

A new variety of Floribunda rose suitable for garden decoration, having flowers of red coloration.

1 Drawing Sheet

Classification: The present invention relates to a new *Rosa hybrida* plant.

Variety denomination: The new plant has the varietal denomination 'ISLE OF VIEW'.

BACKGROUND OF THE INVENTION

This invention relates to a new and distinct variety of Floribunda Rose. It has as its seed parent the variety known as unknown seedling and as its pollen parent the variety known as unknown seedling.

SUMMARY OF THE INVENTION

Among the features which distinguish the new variety from other presently available and commercial rose cultivars known to the inventor are the following combination of characteristics: The plant is a bushy compact plant, suitable for outdoor garden decoration. The plant is fairly disease resistant.

Asexual reproduction of the new variety by budding as performed in Kern County shows that the foregoing and other distinguishing characteristics come true to form and are established and transmitted through succeeding asexual propagations. 'Isle of View' may be asexually propagated by cuttings, budding and grafting. The budding and grafting successfully occurred on the plant/rootstock *Rosa hybrida* cv. 'Dr. Huey' (unpatented).

COMPARISON WITH THE CLOSEST COMMERCIALLY AVAILABLE CULTIVAR

The new variety may be distinguished from its closest commercially available cultivar, 'Europeana' (U.S. Plant Pat. No. 2,540) by the following combination of characteristics: a darker red, on a much more compact growing plant that is more disease resistant.

BRIEF DESCRIPTION OF ILLUSTRATION

The accompanying photograph (FIG. 1) illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (1966) except where common terms of color definition are employed.

DESCRIPTION OF THE NEW VARIETY

The following description is of 2 year-old rose plants of the new variety grown outdoors in Wasco, Calif. in the month of October. Phenotypic expression may vary with environmental, cultural and climatic conditions, as well as differences in conditions of light and soil.

FLOWER

The new variety usually bears its flowers in clusters of three to four per stem. Flowers are borne in regular rounded clusters on strong short stems (about 6 cm to about 8 cm). Outdoors, the plant blooms abundantly and nearly continuously during the growing season. The flowers have a slight spicy fragrance.

BUD

The peduncle is about 6 cm to about 8 cm in length, average caliper, and usually erect. It is usually smooth, with many hairs and prickles. Peduncle color is near between 141b and 141c.

Before the calyx breaks, the bud is about 1.5 cm to about 2 cm in diameter at the widest point, about 2 cm to about 2.5 cm in length, and pointed in shape with a conspicuous neck. The surface of the bud bears some foliaceous appendages, moss tomentum and stipitate glands, usually with slender much cut bristle-like foliaceous parts extending beyond the tip of the bud about one half or more of its length. Bud color is near 45a and 45b.

The sepals are about 3 cm to about 3.5 cm in length and about 1.5 cm to about 1.75 cm in width at the widest point. The outer surface color of the sepal is near between 141c and 141d, the inner surface color of the sepal is near between 141b and 141c and covered edged with fine wooly tomentum; sepal margins are lined with many numerous stipitate glands and hairs.

The receptacle of the flower is of somewhat short to medium (about 3 mm to about 3.5 mm) and somewhat thin to average in caliper. The receptacle is globular in form. Its surface is very smooth with thin walls. The receptacle color is near between 141c and 141d.

As the petals open (after the calyx breaks), the bud is about 3 cm to about 3.5 cm in diameter at the widest point, about 3.5 cm to about 4 cm in length and ovoid in form. The color of the under and upper surfaces of the newly opened petals is near between 45a and 45b.

BLOOM

When fully open, the bloom ranges from about 8 cm to about 10 cm in diameter. Petalage is double with about 25 to 30 petals and about 2 to 4 petaloids irregularly arranged. When fully open, the bloom form is globular, and the petals are loosely undulated with petal edges rolled outward.

PETALS

The substance of the petals is moderately crisp and of moderately thick thickness, with upper surfaces slightly velvety and under surfaces very velvety. The petals are about 5.5 cm to about 7.0 cm in length and about 5.5 cm to about 6.5 cm in width at the widest point. Petal margins are dentate.

The outer petals are moderately ovate in shape with apexes moderately rounded usually slightly notched with two or more notches.

The inner petals are moderately ovate in shape with apexes moderately rounded usually slightly notched with two or more notches.

Petaloids are about 1.5 cm to about 3 cm in length and about 5 cm to about 1.7 cm in width at the widest point. Petaloids are shaped rounded with the upper surface satiny and the lower surface satiny.

NEWLY OPENED FLOWER

The under and upper surface color of the outer petals is near between 45b and 45c. A splash of 155a is apparent.

At the point where the petal attaches, the color is near 45b and 45c. The upper surface color of the outer petals is near between 45b and 45c.

The under and upper surface color of the intermediate petals is near between 45b and 45c.

The under and upper surface color of the inner petals is near between 45b and 45c.

The under and upper surface color of the petaloids are similar in coloration to the upper and under surfaces of the intermediate and inner petals.

The general tonality of the newly opened flower is near between 45b and 45c.

THREE-DAY OLD FLOWER

The under and upper surface color of the outer petals is near between 45b and 45c. A splash of 155a is apparent.

At the point where the petal attaches, the color is near 45b and 45c. The upper surface color of the outer petals is near between 45b and 45c.

The under and upper surface color of the intermediate petals is near between 45b and 45c.

The under and upper surface color of the inner petals is near between 45b and 45c.

The under and upper surface color of the petaloids are similar in coloration to the upper and under surfaces of the intermediate and inner petals.

The general tonality of the three-day-old flower is near between 45b and 45c.

On the spent bloom, the petals usually are somewhat moderately fugacious, often drop off cleanly except for petaloids that persist, fading to near between 44c and 44d, and are not particularly affected by cold, hot, wet, or dry weather.

In October, in Wasco, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 125) and are arranged irregularly about the pistils. The filaments are short to length (about 2 cm to about 2.5 cm) most with anthers. Filaments are near between 14b and 14c in color. The anthers are somewhat small for the class and all open approximately at the same time. Anther color is near 11a when immature and near between 14a and 15a at maturity. Pollen is sparse to moderate and near 23a and 23b in color.

FEMALE REPRODUCTIVE ORGANS

Pistils vary in number (average about 30). The styles are very uneven, moderately short in length, moderately heavy in caliper and are densely bunched. Stigma color is near between 2a and 3a. Style color is near between 1a and 1b. Ovaries are usually enclosed in the calyx.

Hips have not been observed on this variety when grown in Wasco, Calif.

FOILAGE

The compound leaves are usually comprised of five to seven leaflets and are borne abundantly in normal quantities. The five-leaflet leaves are about 4 cm to about 6.5 cm in length and about 3 cm to about 4.5 cm in width at the widest point, moderately leathery to crisp in texture, and glossy in finish. The terminal leaflets are about 6 cm to about 4 cm in length and about 4 cm to about 2 cm in width at the widest point, shaped somewhat oval with very moderately somewhat obtuse to mucronate apexes and have somewhat round bases. Their margins are simply serrate.

The upper and under surface color of the mature leaf is near between 141a and 141b. The upper and under surface color of the young leaf is near between 141c and 141d.

The rachis is light in caliper and smooth. The upper side is moderately grooved with few hairs and stipitate glands and prickles on the edges of the grooves. The under side of the rachis is very smooth with few prickles. The rachis color is near between 147c and 147d.

The stipules are about 1 cm to about 1.5 cm in length and somewhat narrow that turn out at an angle of less than 45 degrees toward the stem.

The petiole is average in caliper and somewhat smooth. The upper side is deeply to moderately grooved with some hairs and stipitate glands and prickles on the edges of the grooves. The under side of the rachis is somewhat smooth with some hairs and stipitate glands and moderately medium prickles. The petiole is about 5 cm to about 6 cm in length and about 2.5 cm to about 6 cm in diameter at the widest point. The petiole color is near 164c and 164d.

The plant displays an average degree of resistance to powdery mildew and rust as compared to other commercial varieties grown under comparable conditions in Upland, Calif. The plant's winter hardiness and drought/heat tolerance are yet to be determined.

GROWTH

The plant has compact low growth habit (about 120 to about 140 cm in height and about 95 cm to about 100 cm spread at the widest point), with moderate branching. It displays vigorous growth and the canes are somewhat light caliper for the class.

The color of the major stems is near between 143b and 143c. The few small prickles that are about 1 cm to about 1.5 cm in length, the small prickles are almost straight; prickle color is near between 173a and 173b. The major stem bears few small prickles of similar shape and coloration and which are near between 173b and 173c in color.

The color of the branches is near between 141b and 141c. They bear few prickles which are of similar size and shape to the prickles on the major stems; prickle color is near between 164c and 164d. The branches bear few small prickles of similar shape and coloration and which are near between 164c and 164d in color.

The color of the new shoots is near between 141c and 141d. They bear few prickles which are of similar size and shape to the prickles on the major stems; prickle color is near 164d.

I claim:

1. A new and distinct Floribunda rose plant of the variety substantially as described and illustrated herein.

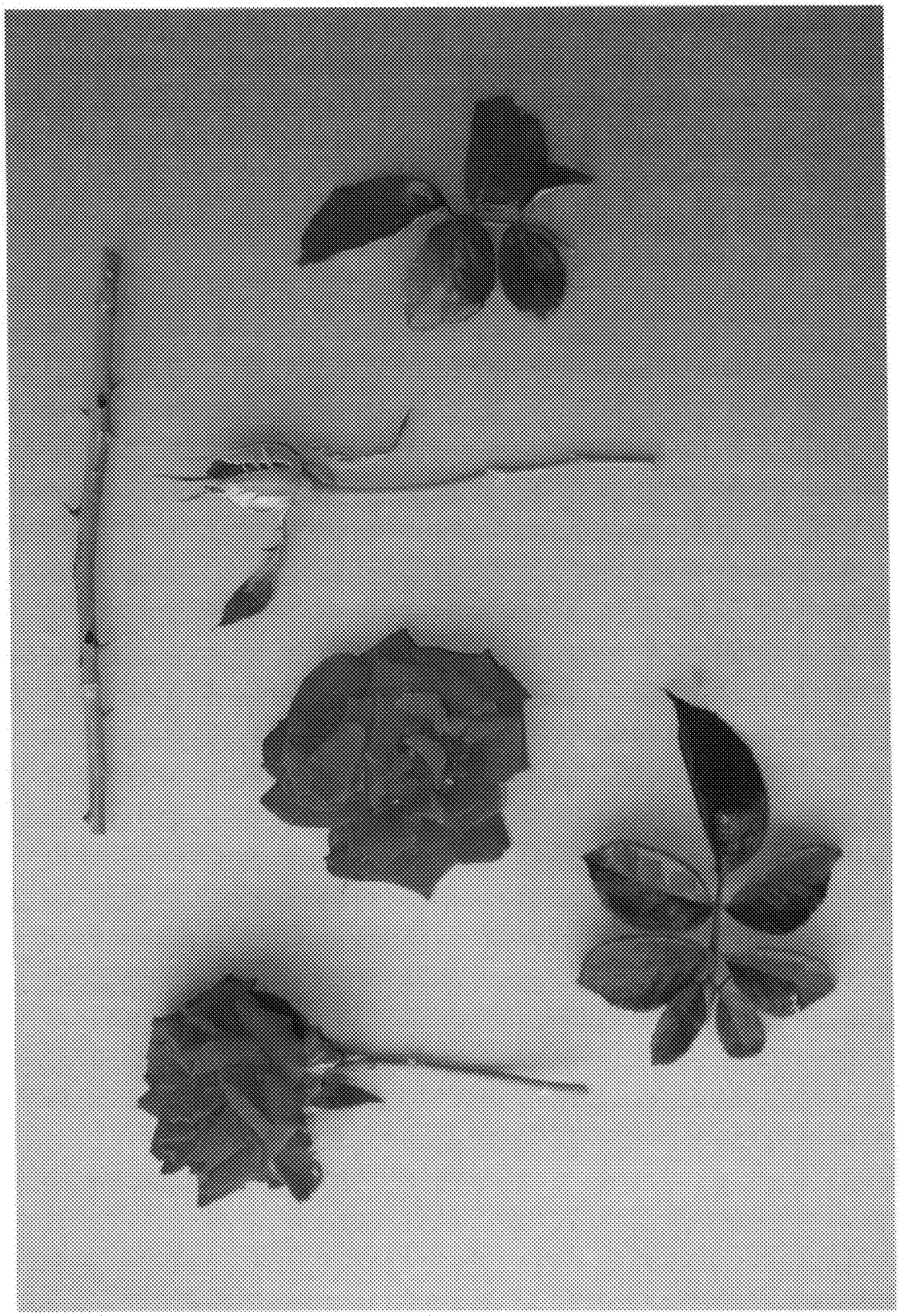

* * * * *